(12) United States Patent
Gore et al.

(10) Patent No.: US 8,119,662 B2
(45) Date of Patent: Feb. 21, 2012

(54) CRYSTALLINE COMPOUNDS

(75) Inventors: Vinayak G. Gore, Maharashtra (IN);
Ashok D. Pehere, Maharashtra (IN);
Avinash C. Gaikwad, Maharashtra (IN);
Priyesh S. Vijaykar, Maharashtra (IN)

(73) Assignee: Generics [UK] Limited (GB)

( * ) Notice: Subject to any disclaimer, the term of this patent is extended or adjusted under 35 U.S.C. 154(b) by 297 days.

(21) Appl. No.: 11/961,695

(22) Filed: Dec. 20, 2007

(65) Prior Publication Data
US 2008/0182888 A1 Jul. 31, 2008

Related U.S. Application Data

(63) Continuation of application No. PCT/GB2006/050179, filed on Jun. 30, 2006.

(30) Foreign Application Priority Data

Jul. 1, 2005 (IN) .......................... 780/MUM/2005

(51) Int. Cl.
*A61K 31/40* (2006.01)
(52) U.S. Cl. ...................................... 514/323
(58) Field of Classification Search ............ 514/423
See application file for complete search history.

(56) References Cited

U.S. PATENT DOCUMENTS

| 4,316,906 A | 2/1982 | Ondetti et al. |
| 6,515,012 B2 | 2/2003 | Giorgi et al. |
| 6,521,760 B1 | 2/2003 | Giorgi et al. |
| 2002/0156293 A1 | 10/2002 | Giorgi et al. |

FOREIGN PATENT DOCUMENTS
WO 00/07984 2/2000

OTHER PUBLICATIONS

Lozano, et al, Temperature, pH and Agitation Rate as Dissolution Test Discriminators of Zofenophril Calcium Tablets, *Journal of Pharmaceutical and Biomedical Analysis*, 1994, vol. 12(2), pp. 173-177.

*Primary Examiner* — Jason Sims
*Assistant Examiner* — Zohreh Vakil
(74) *Attorney, Agent, or Firm* — Dorsey & Whitney LLP

(57) ABSTRACT

The present invention relates to a novel crystalline form of zofenopril calcium of formula (I), chemically known as (4S)-1-[(2S)-3-(benzoylthio)-2-methylpropionyl]-4-(phenylthio)-L-proline calcium salt. The present invention further relates to a process for the preparation of the new crystalline form of zofenopril calcium and its use in pharmaceutical preparations.

Formula (I)

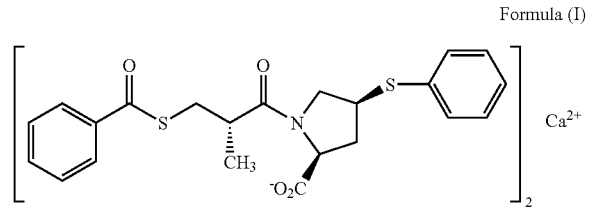

7 Claims, No Drawings

CRYSTALLINE COMPOUNDS

CROSS REFERENCE TO RELATED APPLICATION(S)

This application is a Continuation of International Patent Application PCT/GB2006/050179, filed on Jun. 30, 2006, which claims priority to India Application No. 780/mum/2005, filed on Jul. 1, 2005, the entire contents of both of which are hereby incorporated by reference.

TECHNICAL FIELD

The present invention relates to a novel crystalline form of zofenopril calcium of formula (I), chemically known as (4S)-1-[(2S)-3-(benzoylthio)-2-methylpropionyl]-4-(phenylthio)-L-proline calcium salt.

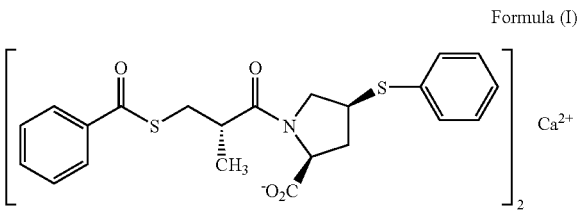

Formula (I)

The present invention further relates to a process for the preparation of the new crystalline form of zofenopril calcium and its use in pharmaceutical preparations.

BACKGROUND ART

Zofenopril is a non-peptidic orally active sulphydryl ACE inhibitor with long lasting action, which is approved for the treatment of hypertension.

U.S. Pat. No. 6,515,012 and U.S. Pat. No. 6,521,760 discuss the prior art disclosed in U.S. Pat. No. 4,316,906 and describe the method for the preparation of zofenopril calcium as disclosed in U.S. Pat. No. 4,316,906 as comprising the following steps: condensation between cis-4-(phenylthio)-L-proline and D-3-(benzoylthio)-2-methylpropionyl chloride in aqueous solution keeping the pH at values of 8-8.5 by addition of 5N sodium hydroxide, subsequent acidification with HCl, extraction with isobutyl acetate and concentration of the extracts, washing with saline solution, to give (4S)-1-[(2S)-3-(benzoylthio)-2-methylpropinoyl]-4-(phenylthio)-L-proline; treatment of the resinous material from the previous step in isopropanol solution with potassium 2-ethylhexanoate to obtain the corresponding potassium salt; dissolution of the potassium salt in water to a 5% concentration and very slow addition, with simultaneous seeding, of a slight excess of a 2N calcium chloride aqueous solution to precipitate the desired calcium salt, washing the resulting product thoroughly with water, drying under vacuum at a comparatively high temperature to give the desired calcium salt as dry powder with a melting point of about 250° C.; alternatively (4S)-1-[(2S)-3-(benzoylthio)-2-methylpropinoyl]-4-(phenylthio)-L-proline is dissolved in ethanol and treated with the same volume of an aqueous suspension containing one equivalent of CaO; after removing ethanol and subsequently washing with ether, the aqueous suspension is freeze-dried to obtain the calcium salt with a melting point of 235-237° C.

According to U.S. Pat. No. 6,515,012 and U.S. Pat. No. 6,521,760, the synthesis described in U.S. Pat. No. 4,316,906 (cited above at points a, b and c) mainly yields polymorph A, but also polymorph B in very variable percentages and never below 20%. Moreover, the alternative synthesis described (cited at point d) affords a partially amorphous product with very variable characteristics, in which polymorph A, when present, is in concentrations much lower than those obtained in the preceding process.

U.S. Pat. No. 6,515,012 and U.S. Pat. No. 6,521,760 both disclose a process for the preparation of substantially pure polymorph A of zofenopril calcium comprising the following steps:

reaction of (S)(−)-3-(benzoylthio)-2-methyl-propanoic acid chloride and cis-4-(phenylthio)-L-proline in water at a pH ranging from 9.0-9.5 and recovery of zofenopril in the acidic form, salification of acid zofenopril with a potassium salt in alcoholic solution and recovery of the resulting potassium salt, conversion of the potassium salt to calcium by addition of an aqueous solution of zofenopril potassium salt to a calcium chloride aqueous solution at 70-90° C. with simultaneous seeding to promote the precipitation of polymorph A.

The synthesis disclosed in the aforesaid US patents for the preparation of polymorph A has the following drawbacks:

The reaction is carried out at a relatively high temperature (80-85° C.) at which inter-conversion of the polymorphs is possible.

Substantially pure polymorph A can be obtained from the above process, but the possibility of traces of polymorph B cannot be ruled out.

The aforesaid US patents also disclose a process for the preparation of polymorph B comprising the following steps:

A solution of zofenopril potassium salt (0.27M) is sprayed in lukewarm water (55° C.), while adding a calcium chloride solution, the solution being such that the total amounts of drug and calcium chloride are equimolar.

The resulting suspension containing the slurry product is heated at 85° C. for 12-14 hours to obtain complete conversion to polymorph B.

After cooling at about 25° C., the product is filtered, washed with water until it is substantially free from chloride ions, and then dried under vacuum.

Both, polymorph A and polymorph B, are anhydrous forms of zofenopril calcium.

The present inventors have developed a process for the preparation of a novel crystalline form of zofenopril calcium, which yields a new crystalline form of zofenopril at relatively milder temperature conditions, thereby preventing the inter-conversion of polymorphs. The novel zofenopril calcium polymorph is called polymorph C and it is a monohydrate form of zofenopril calcium.

The novel crystalline form of zofenopril calcium of the present invention can be used in different dosage forms such as tablets, capsules etc.

OBJECTS OF THE INVENTION

The first object of the present invention is a novel crystalline form of zofenopril calcium, polymorph form C, exhibiting the characteristic XRD pattern outlined in Table 1.

A second object of the present invention is a process for the preparation of the novel crystalline form of zofenopril calcium.

A third object of the present invention is a pharmaceutical preparation containing the novel crystalline form of zofenopril calcium.

A fourth object of the present invention is a method of reducing blood pressure, or treating or preventing hypertension, cardiac decompensation, myocardial infarction, acute myocardial infarction, heart failure or chronic heart failure, comprising administering an effective amount of the novel crystalline form of zofenopril calcium to a patient in need thereof.

A fifth object of the present invention is a use of the novel crystalline form of zofenopril calcium for the manufacture of an ACE inhibitor, or a medicament for reducing blood pressure, or a medicament for treating or preventing hypertension, cardiac decompensation, myocardial infarction, acute myocardial infarction, heart failure or chronic heart failure.

SUMMARY OF THE INVENTION

A first aspect of the present invention provides zofenopril calcium monohydrate.

The first aspect of the present invention further provides zofenopril calcium in polymorph form C.

The first aspect of the present invention further provides zofenopril calcium in crystalline form having inter alia the following characteristic XRD peaks: 4.9, 8.1, 9.1, 9.9, 14.5, 16.0, 17.5, 18.5, 19.0, 20.0, 20.5, 21.5, 22.3, 23.9 and 24.5±0.2 degrees 2θ, or zofenopril calcium in crystalline form having inter alia the following characteristic XRD peaks: 5.1, 8.2, 9.2, 10.0, 14.5, 16.1, 17.5, 18.5, 19.1, 20.1, 20.5, 21.5, 22.4, 24.1 and 24.6±0.2 degrees 2θ.

The zofenopril calcium polymorph of the present invention was found to be particularly suitable for dosage form preparation. The polymorph showed excellent compressibility and other features necessary for dosage form preparation (e.g. tablets). The polymorph also showed excellent stability, with no changes in polymorphic form being detected following grinding and tablet punching.

Preferably the zofenopril calcium polymorph of the present invention comprises less than 10% of zofenopril calcium in other polymorphic forms, preferably less than 5%, more preferably less than 2%, even more preferably less than 1%. Preferably the zofenopril calcium comprises less than 3% of other impurities, more preferably less than 1%, even more preferably less than 0.5%.

The zofenopril calcium can be used as a medicament, for example, as an ACE inhibitor, for reducing blood pressure, or for treating or preventing hypertension, cardiac decompensation, myocardial infarction, acute myocardial infarction, heart failure or chronic heart failure.

Thus according to the first aspect of the present invention there is provided a novel crystalline form of zofenopril calcium, polymorph form C, represented by formula (I) and exhibiting a characteristic XRD pattern as shown in Table 1.

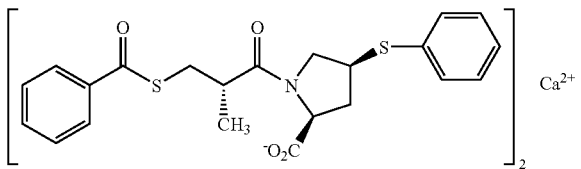

Formula (I)

A second aspect of the present invention provides a process for preparing zofenopril calcium of the present invention, comprising the steps of: adding an aqueous solution of a calcium salt to an aqueous solution of a zofenopril salt, and separating precipitated zofenopril calcium from the mother liquor.

Preferably the zofenopril salt is a zofenopril metal salt. More preferably the zofenopril salt is zofenopril potassium, sodium, lithium, calcium, magnesium or aluminium. Even more preferably, the zofenopril salt is zofenopril potassium.

Preferably the calcium salt is calcium fluoride, chloride, bromide, iodide, oxide, hydroxide, carbonate, nitrate, sulfate or acetate. More preferably the calcium salt is calcium fluoride, chloride, bromide, iodide or oxide. Even more preferably the calcium salt is calcium chloride.

Preferably step (a) is carried out at a temperature of up to 60° C., preferably at a temperature of from 25 to 60° C. In one embodiment, step (a) is carried out at a temperature of from 30 to 60° C., preferably from 40 to 60° C., preferably from 50 to 60° C., preferably from 55 to 60° C. In another embodiment, step (a) is carried out at a temperature of from 25 to 30° C.

Preferably the reaction mixture is maintained at a temperature of up to 60° C. for 2 to 30 hours between steps (a) and (b). In one embodiment, the reaction mixture is maintained at a temperature of from 55 to 60° C. for 2 to 4 hours between steps (a) and (b). In another embodiment, the reaction mixture is maintained at a temperature of from 25 to 30° C. for 20 to 30 hours between steps (a) and (b).

Preferably the reaction mixture is stirred whilst being maintained for 2 to 30 hours between steps (a) and (b).

In one embodiment, precipitation of zofenopril calcium is facilitated by seeding with crystals. However, no seeding with crystals is preferable.

In step (b), zofenopril calcium is preferably separated from the mother liquor by filtration.

Preferably step (b) is carried out at a temperature of up to 60° C., preferably at a temperature of from 25 to 60° C. In one embodiment, step (b) is carried out at a temperature of from 55 to 60° C. In another embodiment, step (b) is carried out at a temperature of from 25 to 30° C.

Preferably the process further comprises the step of washing the zofenopril calcium with water, preferably until the zofenopril calcium is free from chloride ions.

Preferably the process further comprises the step of drying the zofenopril calcium. Preferably the zofenopril calcium is dried under reduced pressure. Preferably the zofenopril calcium is dried at a temperature of up to 60° C., preferably at a temperature of from 40 to 60° C., preferably at a temperature of about 50° C. Preferably the zofenopril calcium is dried until the moisture content falls below about 1%, preferably below about 0.5%.

Preferably the temperature is kept at 60° C. or less substantially throughout the process. For the purposes of the present invention, the temperature is kept at 60° C. or less 'substantially throughout the process', even if the temperature occasionally rises above 60° C., provided this rise in temperature does not influence the polymorphic form of the zofenopril calcium obtained.

Thus according to the second aspect of the present invention there is provided a process for the preparation of a novel crystalline form of zofenopril calcium.

A third aspect of the present invention provides a pharmaceutical composition, comprising zofenopril calcium of the present invention. Preferably the pharmaceutical composition further comprises a pharmaceutically acceptable carrier, excipient or diluent.

Preferably the pharmaceutical composition is suitable for oral or parenteral administration. Preferably the pharmaceutical composition is in the form of a tablet, capsule, syrup, suspension or elixir for oral administration or in the form of a sterile solution or suspension for parenteral administration.

Preferably the pharmaceutical composition is in unit dosage form comprising zofenopril calcium in an amount of from 1 mg to 500 mg, preferably from 2 mg to 200 mg, preferably from 3 mg to 100 mg, more preferably from 4 mg to 60 mg. The unit dosage form can be administered once, twice, three times or four times daily.

Preferably the pharmaceutical composition is suitable for use as an ACE inhibitor, for reducing blood pressure, or for treating or preventing hypertension, cardiac decompensation, myocardial infarction, acute myocardial infarction, heart failure or chronic heart failure.

A fourth aspect of the present invention provides a method of reducing blood pressure, or of treating or preventing hypertension, cardiac decompensation, myocardial infarction, acute myocardial infarction, heart failure or chronic heart failure, comprising administering an effective amount of zofenopril calcium of the present invention to a patient in need thereof. Preferably the patient is a mammal, more preferably a human. Preferably the amount of zofenopril calcium administered is from 0.1 mg to 100 mg per kg per day, preferably from 1 mg to 15 mg per kg per day.

A fifth aspect of the present invention provides a use of zofenopril calcium of the present invention for the manufacture of an ACE inhibitor, a medicament for reducing blood pressure, or a medicament for treating or preventing hypertension, cardiac decompensation, myocardial infarction, acute myocardial infarction, heart failure or chronic heart failure.

DETAILED DESCRIPTION OF THE INVENTION

The novel crystalline form of zofenopril calcium of the present invention can be prepared by the following procedure:

To an aqueous solution of zofenopril potassium salt, an aqueous solution of calcium chloride is added at 55-60° C. and the resulting suspension is stirred for three hours. Then this suspension is filtered off at 55° C. and the product is washed by water until free from chloride ions.

The wet solids are dried under reduced pressure at 50° C. until the moisture content falls below 0.5%.

The XRD pattern of the product thus obtained, polymorph C, is different from the reported polymorph A and polymorph B of zofenopril calcium as represented in Table 1.

TABLE 1

XRD Comparison Position [2θ values]

| Polymorph A (WO 00/07984) | Polymorph B (WO 00/07984) | New Polymorph C (prepared at 55-60° C. and dried at 50° C.) | New Polymorph C (prepared at 25-30° C. and dried at 25-30° C.) |
|---|---|---|---|
| 4.3 | | | |
| | 4.8 | | |
| | | 4.9 | 5.1 |
| 7.4 | | | |
| | | 8.1 | 8.2 |
| 8.7 | | | |
| | | 9.1 | 9.2 |
| | | 9.9 | 10.0 |
| 10.1 | | | |
| 10.8 | | | |
| 11.7 | | | |
| 13.0 | | | |
| | | 14.5 | 14.5 |
| 14.8 | | | |
| | 15.6 | | |
| 16.0 | | 16.0 | 16.1 |
| 17.2 | | | |
| | | 17.5 | 17.5 |
| 18.2 | | | |
| | 18.5 | 18.5 | 18.5 |
| 19.0 | | 19.0 | 19.1 |
| | 19.4 | | |
| 20.0 | | 20.0 | 20.1 |
| | 20.5 | 20.5 | 20.5 |
| | 21.4 | 21.5 | 21.5 |
| 21.7 | | | |
| | 21.8 | | |
| | | 22.3 | 22.4 |
| | 23.1 | | |
| 23.5 | | | |
| | | 23.9 | 24.1 |
| 24.6 | 24.6 | 24.5 | 24.6 |

The temperature employed in the process for the preparation of the novel crystalline form of zofenopril calcium is 60° C. or less, preferably from 30-60° C., preferably from 55-60° C.

The novel crystalline form of zofenopril calcium of the present invention can be utilized to achieve a reduction of blood pressure by formulating in compositions such as tablets, capsules, syrups, suspensions or elixirs for oral administration or in sterile solutions or suspensions for parenteral administration.

Additional excipients conventionally known in the art, such as carriers, binders, preservatives, stabilizers, flavours, disintegrants and lubricants etc., may be incorporated.

The following paragraphs enumerated consecutively from 1 through 47 provide for various aspects of the present invention. In one embodiment, in a first paragraph (1), the present invention provides:

Zofenopril calcium monohydrate.
Zofenopril calcium in polymorph form C.
Zofenopril calcium in crystalline form having inter alia the following characteristic XRD peaks: 4.9, 8.1, 9.1, 9.9, 14.5, 16.0, 17.5, 18.5, 19.0, 20.0, 20.5, 21.5, 22.3, 23.9 and 24.5±0.2 degrees 2θ.
Zofenopril calcium in crystalline form having inter alia the following characteristic XRD peaks: 5.1, 8.2, 9.2, 10.0, 14.5, 16.1, 17.5, 18.5, 19.1, 20.1, 20.5, 21.5, 22.4, 24.1 and 24.6±0.2 degrees 2θ.
Zofenopril calcium as described in any one of the preceding paragraphs, wherein the zofenopril calcium comprises less than 10% of zofenopril calcium in other polymorphic forms.
Zofenopril calcium as described in any one of the preceding paragraphs, wherein the zofenopril calcium comprises less than 3% of impurities other than zofenopril calcium in other polymorphic forms.
Zofenopril calcium as described in any one of the preceding paragraphs, for use as a medicament.
Zofenopril calcium as described in any one of the preceding paragraphs, for use as an ACE inhibitor.
Zofenopril calcium as described in any one of the preceding paragraphs, for reducing blood pressure.

Zofenopril calcium as described in any one of the preceding paragraphs, for treating or preventing hypertension, cardiac decompensation, myocardial infarction, acute myocardial infarction, heart failure or chronic heart failure.

A process for preparing zofenopril calcium as described in any one of paragraphs 1 to 10 comprising the steps of:
adding an aqueous solution of a calcium salt to an aqueous solution of a zofenopril salt, and
separating precipitated zofenopril calcium from the mother liquor.

A process as described in paragraph 11, wherein the zofenopril salt is a zofenopril metal salt.

A process as described in paragraph 12, wherein the zofenopril salt is zofenopril potassium, sodium, lithium, calcium, magnesium or aluminium.

A process as described in paragraph 13, wherein the zofenopril salt is zofenopril potassium.

A process as described in any one of paragraphs 11 to 14, wherein the calcium salt is calcium fluoride, chloride, bromide, iodide, oxide, hydroxide, carbonate, nitrate, sulfate or acetate.

A process as described in paragraph 15, wherein the calcium salt is calcium chloride.

A process as described in any one of paragraphs 11 to 16, wherein step (a) is carried out at a temperature of up to 60° C.

A process as described in any one of paragraphs 11 to 17, wherein the reaction mixture is maintained at a temperature of up to 60° C. for 2 to 30 hours between steps (a) and (b).

A process as described in paragraph 18, wherein the reaction mixture is maintained at a temperature of from 55 to 60° C. for 2 to 4 hours between steps (a) and (b).

A process as described in paragraph 18, wherein the reaction mixture is maintained at a temperature of from 25 to 30° C. for 20 to 30 hours between steps (a) and (b).

A process as described in any one of paragraphs 18 to 20, wherein the reaction mixture is stirred whilst being maintained for 2 to 30 hours between steps (a) and (b).

A process as described in any one of paragraphs 11 to 21, wherein in step (b) zofenopril calcium is separated from the mother liquor by filtration.

A process as described in any one of paragraphs 11 to 22, wherein step (b) is carried out at a temperature of up to 60° C.

A process as described in any one of paragraphs 11 to 23, further comprising the step of washing the zofenopril calcium with water.

A process as described in paragraph 24, wherein the zofenopril calcium is washed with water until free from chloride ions.

A process as described in any one of paragraphs 11 to 25, further comprising the step of drying the zofenopril calcium.

A process as described in paragraph 26, wherein the zofenopril calcium is dried under reduced pressure.

A process as described in paragraph 26 or 27, wherein the zofenopril calcium is dried at a temperature of up to 60° C.

A process as described in any one of paragraphs 26 to 28, wherein the zofenopril calcium is dried until the moisture content falls below about 1%.

A process as described in paragraph 29, wherein the zofenopril calcium is dried until the moisture content falls below about 0.5%.

A process as described in any one of paragraphs 11 to 30, wherein the temperature is kept at 60° C. or less substantially throughout the process.

A pharmaceutical composition, comprising zofenopril calcium as described in any one paragraphs 1 to 10.

A pharmaceutical composition as described in paragraph 32, further comprising a pharmaceutically acceptable carrier, excipient or diluent.

A pharmaceutical composition as described in paragraph 32 or 33, wherein the composition is for oral or parenteral administration.

A pharmaceutical composition as described in any one of paragraphs 32 to 34, wherein the composition is in the form of a tablet, capsule, syrup, suspension or elixir for oral administration or in the form of a sterile solution or suspension for parenteral administration.

A pharmaceutical composition as described in any one of paragraphs 32 to 35, wherein the composition is in unit dosage form comprising zofenopril calcium in an amount of from 1 mg to 500 mg.

A pharmaceutical composition as described in any one of paragraphs 32 to 36, for use as an ACE inhibitor.

A pharmaceutical composition as described in any one of paragraphs 32 to 37, for reducing blood pressure.

A pharmaceutical composition as described in any one of paragraphs 32 to 38, for treating or preventing hypertension, cardiac decompensation, myocardial infarction, acute myocardial infarction, heart failure or chronic heart failure.

A method of reducing blood pressure, comprising administering an effective amount of zofenopril calcium as described in any one of paragraphs 1 to 10 to a patient in need thereof.

A method of treating or preventing hypertension, cardiac decompensation, myocardial infarction, acute myocardial infarction, heart failure or chronic heart failure, comprising administering an effective amount of zofenopril calcium as described in any one of paragraphs 1 to 10 to a patient in need thereof.

A method as described in paragraph 40 or 41, wherein the patient is a mammal.

A method as described in paragraph 42, wherein the patient is a human.

A method as described in any one of paragraphs 40 to 43, wherein the amount of zofenopril calcium administered is from 0.1 mg to 100 mg per kg per day.

Use of zofenopril calcium as described in any one of paragraphs 1 to 10 for the manufacture of an ACE inhibitor.

Use of zofenopril calcium as described in any one of paragraphs 1 to 10 for the manufacture of a medicament for reducing blood pressure.

Use of zofenopril calcium as described in any one of paragraphs 1 to 10 for the manufacture of a medicament for treating or preventing hypertension, cardiac decompensation, myocardial infarction, acute myocardial infarction, heart failure or chronic heart failure.

The details of the invention, its objects and advantages are explained hereunder in greater detail in relation to non-limiting exemplary illustrations.

EXAMPLE 1

To an aqueous solution of zofenopril potassium salt, an aqueous solution of calcium chloride was added at 55-60° C. and the resulting suspension was stirred for three hours. Then this suspension was filtered at 55° C. and the product was washed by water until free from chloride ions. The wet solids were dried under reduced pressure at 50° C. until the moisture content fell below 0.5%. The zofenopril calcium thus obtained was found to have a melting point of 244-248° C.

and a chemical purity of 99.5% as measured by HPLC. The zofenopril calcium was in monohydrate form.

EXAMPLE 2

To an aqueous solution of zofenopril potassium salt, an aqueous solution of calcium chloride was added at 25-30° C. The temperature of the reaction mixture was maintained for 24 hours. Then this suspension was filtered at 25° C. and the product was washed by water until free from chloride ions. The wet solids were dried under reduced pressure at 50° C. until the moisture content fell below 0.5%. The zofenopril calcium thus obtained was found to have a melting point of 244-248° C. and a chemical purity of 99.7% as measured by HPLC. The zofenopril calcium was in monohydrate form.

It will be understood that the present invention has been described above by way of example only. The examples are not intended to limit the scope of the invention. Various modifications and embodiments can be made without departing from the scope and spirit of the invention, which is defined by the following claims only.

What is claimed is:

1. Zofenopril calcium monohydrate.

2. Zofenopril calcium in crystalline form having the following characteristic XRD peaks: 4.9±0.2, 8.1±0.2, 9.1±0.2, 9.9±0.2, 14.5±0.2, 16.0±0.2, 17.5±0.2, 18.5±0.2, 19.0±0.2, 20.0±0.2, 20.5±0.2, 21.5±0.2, 22.3±0.2, 23.9±0.2 and 24.5±0.2 degrees 2θ.

3. Zofenopril calcium in crystalline form having the following characteristic XRD peaks: 5.1±0.2, 8.2±0.2, 9.2±0.2, 10.0±0.2, 14.5±0.2, 16.1±0.2, 17.5±0.2, 18.5±0.2, 19.1±0.2, 20.1±0.2, 20.5±0.2, 21.5±0.2, 22.4±0.2, 24.1±0.2 and 24.6±0.2 degrees 2θ.

4. Zofenopril calcium as claimed in claim 1, wherein the zofenopril calcium comprises:
    (a) less than 10% of zofenopril calcium in other polymorphic forms; and/or
    (b) less than 3% of impurities other than zofenopril calcium in other polymorphic forms.

5. A pharmaceutical composition, comprising zofenopril calcium monohydrate, or zofenopril calcium in polymorph form C, or zofenopril calcium in crystalline form having the following characteristic XRD peaks: 4.9±0.2, 8.1±0.2, 9.1±0.2, 9.9±0.2, 14.5±0.2, 16.0±0.2, 17.5±0.2, 18.5±0.2, 19.0±0.2, 20.0±0.2, 20.5±0.2, 21.5±0.2, 22.3±0.2, 23.9±0.2 and 24.5±0.2 degrees 2θ, or zofenopril calcium in crystalline form having the following characteristic XRD peaks: 5.1±0.2, 8.2±0.2, 9.2±0.2, 10.0±0.2, 14.5±0.2, 16.1±0.2, 17.5±0.2, 18.5±0.2, 19.1±0.2, 20.1±0.2, 20.5±0.2, 21.5±0.2, 22.4±0.2, 24.1±0.2 and 24.6±0.2 degrees 2θ, or mixtures thereof, and a pharmaceutically acceptable carrier, excipient or diluent.

6. A pharmaceutical composition as claimed in claim 5, wherein the composition is in the form of a tablet, capsule, syrup, suspension or elixir for oral administration or in the form of a sterile solution or suspension for parenteral administration.

7. A pharmaceutical composition as claimed in claim 5, wherein the composition is in unit dosage form comprising zofenopril calcium in an amount of from 1 mg to 500 mg.

* * * * *